United States Patent [19]

Sanchez

[11] Patent Number: 4,851,418

[45] Date of Patent: Jul. 25, 1989

[54] NAPHTHYRIDINE ANTIBACTERIAL AGENTS CONTAINING AN α-AMINO ACID IN THE SIDE CHAIN OF THE 7-SUBSTITUENT

[75] Inventor: Joseph P. Sanchez, Canton, Mich.

[73] Assignee: Warner-Lambert Company, Morris Plains, N.J.

[21] Appl. No.: 220,177

[22] Filed: Jul. 20, 1988

Related U.S. Application Data

[63] Continuation-in-part of Ser. No. 87,950, Aug. 21, 1987, abandoned.

[51] Int. Cl.$^4$ .................... A61K 31/44; C07D 471/04
[52] U.S. Cl. .................................. 514/300; 540/579; 544/349; 544/362; 544/363; 546/123; 546/126; 546/156
[58] Field of Search .................. 546/123; 514/300

[56] References Cited

PUBLICATIONS

Egawa et al., J. Med. Chem., vol. 27, pp. 1543–1548, (1984).

*Primary Examiner*—Mary C. Lee
*Assistant Examiner*—Bernard I. Dentz
*Attorney, Agent, or Firm*—Ronald A. Daignault

[57] ABSTRACT

Novel quinolone and naphthyridine antibacterial agents are herein described having improved in vivo activity both orally and subcutaneously where the 7-side chain of such compounds contain an α-amino acid; also described are its corresponding optical isomers, methods of preparation as well as compositions and methods of treating infections diseases.

27 Claims, No Drawings

NAPHTHYRIDINE ANTIBACTERIAL AGENTS CONTAINING AN α-AMINO ACID IN THE SIDE CHAIN OF THE 7-SUBSTITUENT

CROSS-REFERENCE TO RELATED APPLICATION

This is a continuation-in-part of U.S. application Ser. No. 087,950, filed Aug. 21, 1987, now abandoned.

BACKGROUND OF THE INVENTION 7-amino-6-fluoro- and 7-amino-6,8-difluoro quinolone-3-carboxylic acids and 7-amino-6-fluoro-1,8-naphthyridine-3-carboxylic acids are especially known to have potent antibacterial activity especially in vitro against gram-negative bacteria. Corresponding 7-amino-pyrrolidinyl-quinolones and naphthyridines of the above type have shown to extend this potent activity against gram-positive bacteria. Nevertheless, many of the above compounds do not exhibit potent activity when tested in vivo. It has now been found that by adding an α-amino acid to the known 7-amino substituents, there is surprisingly enhanced in vivo antibacterial activity when such compounds are administered both orally and subcutaneously.

SUMMARY OF THE INVENTION

Accordingly, the present invention relates to novel quinolones and naphthyridines having the formula

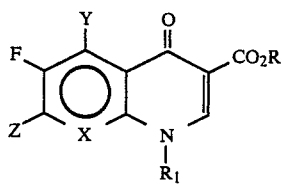

I wherein
X is N, CH, CF, CCl, CCF$_3$, COR$_2$, or CNR$_2$R$_3$;
Y is H, F, NH$_2$, or OR$_2$;
Z is

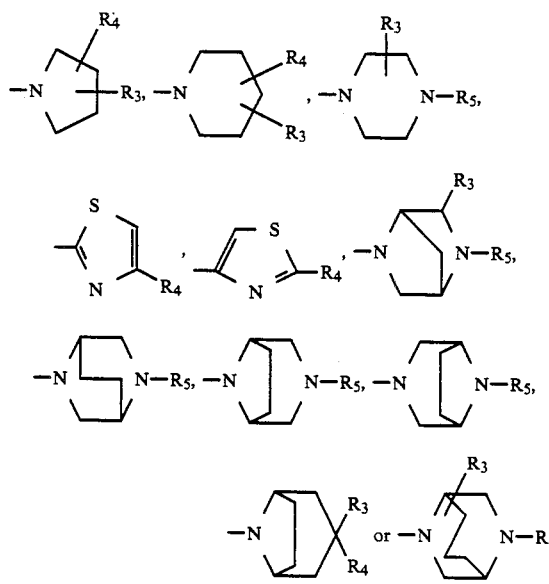

R is H, alkyl of 1–6 carbon atoms or a cation;

R$_1$ is alkyl of 1–6 carbon atoms, haloalkyl in which alkyl has 1–4 carbon atoms, vinyl, cycloalkyl of 3–6 carbon atoms, aryl or aryl substituted by halogen, hydroxy, amino, or alkyl of 1–14 carbon atoms;
R$_2$ and R$_3$ are each independently hydrogen or alkyl of 1–4 carbon atoms;
R$_4$ is —(CR$_2$R$_3$)$_n$—NR$_2$R$_5$ in which n is 0, 1 or 2; and
R$_5$ is

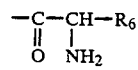

in which R$_6$ is hydrogen, alkyl of 1–10 carbon atoms, alkyl of 1–10 carbon atoms substituted by OR$_2$, NR$_2$R$_3$, CO$_2$H, CO$_2$R$_2$, CONR$_2$R$_3$,

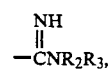

SR$_2$,

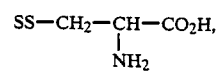

CN, aryl, or aryl substituted by halogen, hydroxy, amino, or alkyl of 1–4 carbon atoms, or phenyl, p-hydroxyphenyl, or taken with the nitrogen atom of the α-amino group is trimethylene or hydroxy substituted trimethylene; an optically active isomer thereof, or a pharmaceutically acceptable acid addition salt, thereof.

A second aspect of the present invention is a pharmaceutical composition comprising an anti-bacterially effective amount of a compound of formula I together with a carrier or excipient.

A third aspect of the present invention is a method of treating bacterial infections comprising administering to a host suffering therefrom a pharmaceutical composition containing a compound of formula I in unit dosage form.

DETAILED DESCRIPTION OF PREFERRED EMBODIMENTS

The present invention essentially concerns α-amino acid derivatives on the side chain of known 7-aminoquinolone and naphthyridine antibacterial agents.

By α-amino acids, the invention includes all naturally occurring α-amino acids, their D-conformers, and additional analogs as defined by the group R$_5$ below. The naturally occurring α-amino acids are glycine, alanine, valine, leucine, isoleucine, phenylalanine, asparagine, glutamine, tryptophan, proline, serine, threonine, tyrosine, hydroxyproline, cysteine, cystine, methionine, aspartic acid, glutamic acid, lysine, arginine, and histidine.

The additional parameters under the compounds of formula I are hereinafter defined.

"Alkyl" is a straight or branched hydrocarbon chain having a designated number of carbon atoms. Thus "alkyl" may include methyl, ethyl, n-propyl, isopropyl, n-butyl, isobutyl, sec-butyl, t-butyl, amyl, hexyl, decyl, and the like.

The term "halo" or "halogen" means an atom of the halogen series such as fluorine, chlorine, bromine, and iodine. The preferred halogens are fluorine or chlorine.

"Cycloalkyl" refers to a saturated cyclic hydrocarbon group such as cyclopropyl, cyclobutyl, cyclopentyl, and cyclohexyl. The preferred cycloalkyl group is cyclopropyl.

The term "aryl" contemplates any aromatic or heteroaromatic ring or fused ring and this includes a "5- or 6-membered heterocyclic ring containing at least one nitrogen, oxygen, or sulfur atom" such as 2-, 3-, or 4-pyridine, 2- or 3-thiophene, 2- or 3-furan, 2-imidazole, 2-oxazole, 2-thiazole and the like.

In addition to the customary and preferred phenyl group, "aryl" also includes naphthyl, indanyl, indolyl, quinolyl, isoquinolyl and the like.

Also in the definition of the α-amino acyl group $R_5$ as $$-\underset{\underset{O}{\|}}{C}-\underset{\underset{NH_2}{|}}{CH}-R_6$$

$R_6$ is also defined as trimethylene or hydroxy-substituted trimethylene when taken together with the nitrogen atom of the α-amino group so that one terminal methylene is bonded to the α-amino group to form acyl groups derived from proline or hydroxy-proline, both naturally occurring amino acids.

Preferred compounds of the present invention are those of formula I as defined above but in which $R_6$ is hydrogen, alkyl of 1–10 carbon atoms or alkyl of 1–10 carbon atoms substituted by $OR_2$, $NR_2R_3$, $CO_2H$, $CO_2R_2$, $CONR_2R_3$, $$\underset{\underset{CNR_2R_3}{\|}}{NH}$$

$SR_2$, $$SS-\underset{\underset{NH_2}{|}}{CH_2CHCO_2H},$$

CN, phenyl, phenyl substituted by halogen, hydroxy, amino, or alkyl of 1–4 carbon atoms, 3-indolyl or a 5- or 6-membered heterocyclic ring containing at least one nitrogen, oxygen, or sulfur atom, or phenyl, p-hydroxyphenyl, or taken with the nitrogen atom of the α-amino group is trimethylene or hydroxy substituted trimethylene.

Also preferred are compounds of formula I in which $R_6$ is hydrogen, alkyl of 1–4 carbon atoms or alkyl of 1–4 carbon atoms substituted by OH, $NH_2$, $CO_2H$, $CONH_2$, $$\underset{\underset{C-NH_2}{\|}}{NH}$$

$SR_2$, $$-SS-\underset{\underset{NH_2}{|}}{CH_2CHCO_2H},$$

phenyl, p-hydroxyphenyl, 3-indolyl, 4-imidazolyl, or phenyl, p-hydroxyphenyl, or taken with the nitrogen of the α-amino group is trimethylene or hydroxy substituted trimethylene.

Still more preferred are compounds of formula I wherein $R_1$ is alkyl of 1–3 carbon atoms, 2-fluoroethyl, vinyl, cyclopropyl, phenyl, phenyl substituted by halogen, hydroxy, amino or alkyl of 1–4 carbon atoms, or a 5- or 6-membered heteroarometic ring containing at least one nitrogen, oxygen, or sulfur atom.

Further preferred are compounds of formula I wherein X is N, CH, CF, CCl or $CCF_3$; Y is H or $NH_2$, and $R_1$ is ethyl, 2-fluoroethyl, vinyl, or cyclopropyl.

Most preferred of the compounds of the present invention are those wherein Z is $$-N\underset{}{\overset{}{\diagdown}}\hspace{-1em}\underset{}{\overset{R_4}{\diagup}}R_3$$

and $R_1$ is cyclopropyl.

Particularly valuable are the following:

7-[3-[(2-amino-1-oxopropyl)amino]-1-pyrrolidinyl]-1-cyclopropyl-6-fluoro-1,4-dihydro-4-oxo-1,8-naphthyridine-3-carboxylic acid or an optical isomer thereof;

7-[3-[(aminoacetyl)amino]-1-pyrrolidinyl]-1-cyclopropyl-6-fluoro-1,4-dihydro-4-oxo-1,8-naphthyridine-3-carboxylic acid or an optical isomer thereof;

7-[3-[(2-amino-1-oxo-3-phenylpropyl)amino]-1-pyrrolidinyl]-1-cyclopropyl-6-fluoro-1,4-dihydro-4-oxo-1,8-naphthyridine-3-carboxylic acid or an optical isomer thereof;

[S-(R*,S*)]-7-[3-[(2-amino-1-oxo-3-phenylpropyl)amino]-1-pyrrolidinyl]-1-cyclopropyl-6-fluoro-1,4-dihydro-4-oxo-1,8-naphthyridine-3-carboxylic acid or an optical isomer thereof;

7-[3-[(2,5-diamino-1,5-dioxopentyl)amino]-1-pyrrolidinyl]-1-cyclopropyl-6-fluoro-1,4-dihydro-4-oxo-1,8-naphthyridine-3-carboxylic acid or an optical isomer thereof;

7-[3-[(2-amino-4-carboxy-1-oxobutyl)amino]-1-pyrrolidinyl]-1-cyclopropyl-6-fluoro-1,4-dihydro-4-oxo-1,8-naphthyridine-3-carboxylic acid or an optical isomer thereof;

7-[3-[(2,6-diamino-1-oxohexyl)amino]-1-pyrrolidinyl]-1-cyclopropyl-6-fluoro-1,4-dihydro-4-oxo-1,8-naphthyridine-3-carboxylic acid or an optical isomer thereof;

7-[3-[(aminophenylacetyl)amino]-1-pyrrolidinyl]-1-cyclopropyl-6-fluoro-1,4-dihydro-4-oxo-1,8-naphthyridine-3-carboxylic acid or an optical isomer thereof;

7-[3-[[(2-amino-1-oxo-3-phenylpropyl)amino]-methyl]-3-methyl-1-pyrrolidinyl]-1-cyclopropyl-6-fluoro-1,4-dihydro-4-oxo-1,8-naphthyridine-3-carboxylic acid or an optical isomer thereof;

7-[3-[[(2-amino-1-oxopropyl)amino]methyl]-3-methyl-1-pyrrolidinyl]-1-cyclopropyl-6-fluoro-1,4-dihydro-4-oxo-1,8-naphthyridine-3-carboxylic acid or an optical isomer thereof;

7-[3-[[(aminoacetyl)amino]methyl]-3-methyl-1-pyrrolidinyl]-1-cyclopropyl-6-fluoro-1,4-dihydro-4-oxo-1,8-naphthyridine-3-carboxylic acid or an optical isomer thereof;

7-[3-[[(aminophenylacetylamino)methyl]-3-methyl-1-pyrrolidinyl]-1-cyclopropyl-6-fluoro-1,4-dihydro-4-oxo-1,8-naphthyridine-3-carboxylic acid or an optical isomer thereof;

7-[3-[[(2-amino-4-carboxy-1-oxobutylamino]-methyl]-3-methyl-1-pyrrolidinyl]-1-cyclopropyl-6-fluoro-1,4-dihydro-4-oxo-1,8-naphthyridine-3-carboxylic acid or an optical isomer thereof;

7-[3-[[(2,6-diamino-1-oxohexyl)amino]methyl]-3-methyl-1-pyrrolidinyl]-1-cyclopropyl-6-fluoro-1,4-dihydro-4-oxo-1,8-naphthyridine-3-carboxylic acid or an optical isomer thereof;

7-[3-[[(2,5-diamino-1,5-dioxopentylamino]methyl]-3-methyl-1-pyrrolidinyl]-1-cyclopropyl-6-fluoro-1,4-dihydro-4-oxo-1,8-naphthyridine-3-carboxylic acid or an optical isomer thereof;

7-[3-[(2-amino-1-oxopropyl)amino]-1-pyrrolidinyl]-1-cyclopropyl-6,8-difluoro-1,4-dihydro-4-oxo-3-quinolinecarboxylic acid or an optical isomer thereof;

[S-(R*,S*)]-7-[3-[(2-amino-1-oxopropyl)amino]-1-pyrrolidinyl]-1-cyclopropyl-6,8-difluoro-1,4-dihydro-4-oxo-3-quinolinecarboxylic acid or an optical isomer thereof;

The compounds of the present invention and of formula I may be prepared by reacting a compound of the formula

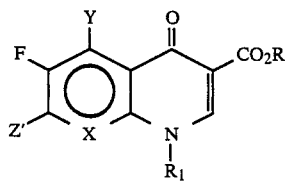

in which Z' is

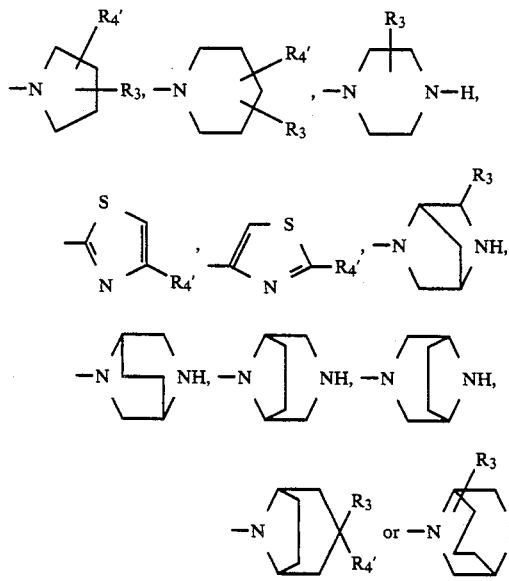

and $R_4'$ is $-(CR_2R_3)_n-NR_2H$, with a compound of the formula

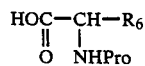

or an activated acid thereof in which Pro represents a protecting group, in the presence of activated acid, and removing the protecting group by acid hydrolysis or catalytic hydrogenation, and, if desired, converting by known means the resulting product to a pharmaceutically acceptable base or acid addition salt thereof.

The quinolones and naphthyridines of formula II having a free primary or secondary amino group are reacted with an α-amino acid by a coupling reaction where the α-amino group is protected by a known amino protecting group, such as carboxylic acyl groups, alkoxycarbonyl groups such as t-butyloxycarbonyl, and benzyloxycarbonyl, and the carboxylic acid group of the α-amino group is left untouched or activated as an acid halide, preferably chloride, a mixed anhydride or a hydroxy succinic ester. A coupling reaction activator such a dicyclohexylcarbodiimide may be used when the carboxylic acid group of that amino acid is used as such. The reaction proceeds as well described in peptide synthesis at a temperature of about 0° to about 100° C. in an inert solvent, such as acetonitrile, chloroform, dichloromethane, or dimethylformamide and, optionally, in the presence of a proton acceptor such a base, e.g., triethylamine or other amine bases.

Following the above reaction, the amino protecting group is removed by known procedures. Alkoxycarbonyl groups, for example, are removed by acid or base hydrolysis and benzyloxycarbonyl, by hydrogenolysis.

An alternative method for preparing the compounds of the present invention when Z is

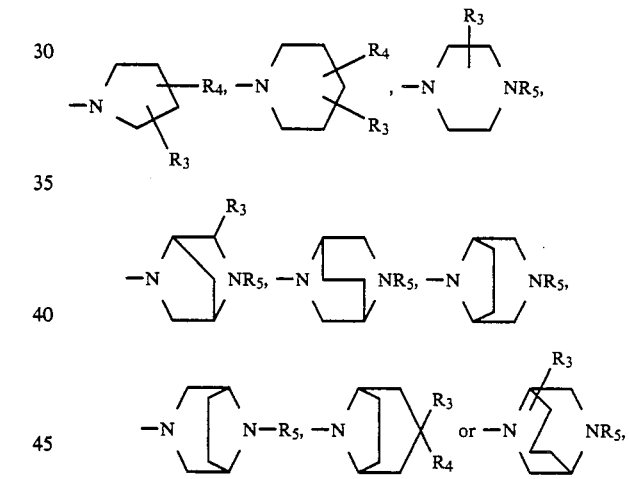

involves reacting a compound of the formula

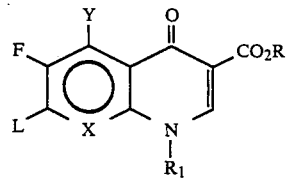

in which L is a leaving group, with an amine of the formula ZH, in which the α-amino group in $R_5$ is protected, and removing the protecting group by acid hydrolysis or catalytic hydrogenation, and, if desired, converting the resulting compound to a pharmaceutically acceptable base or acid addition salt thereof by known means.

The reaction between the compound of formula III and suitably protected ZH may be performed in an inert solvent preferably at elevated temperatures for a sufficient time for the reaction to proceed substantially to completion. The reaction is carried out preferably in the presence of an acid acceptor such an alkali metal or alkaline earth metal carbonate or bicarbonate, a tertiary amine such as triethylamine, pyridine, 1,5-diazabicyclo[5.4.0]-undecene-5 (DBU), or picoline.

Convenient solvents for this reaction are nonreactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually required shorter reaction times.

The removal of the protecting group may be accomplished as mentioned above either in situ or after isolating the product, I.

Because of the presence of an α-amino acid group on the compounds of the present invention, they all exist in optically active forms. The pure D isomer, pure L isomer as well as mixtures thereof, including the racemic mixtures, are contemplated by the invention. The individual D and L isomers are preferably prepared by using the naturally occurring L-α-amino acids or their D-conformers and, in the case of other α-amino acids, resolving such acids by known means, then reacting them by already described methods in standard peptide chemistry, with compounds of the formula II or with an optionally protected amine Z'H, where Z' is above defined.

An additional asymmetric carbon atom may be present in the Z' portion of the compounds of formula II. Thus the compounds of formula I may have two asymmetric carbon atoms and four optical isomers where both asymmetric carbon atoms reside in the Z group. All such isomers, diastereomers, enantiomers as well as mixtures thereof are intended to be included in the invention. The preferable method of synthesizing the individual optical isomers involve preparing the pure isomers in the Z group by reacting the optically active protected α-amino acid with an optically active Z'H to form ZH which is then reacted as described above with a compound of formula III followed by removal of the protecting group.

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, silver, and the like. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formations are hydrochloric, sulfuric, phosphoric, acetic, citric, oxalic, malonic, salicylic, malic, gluconic, fumaric, succinic, ascorbic, maleic, methanesulfonic, lactic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

Starting materials used to prepare compounds of formula I such as compounds of formulae II, III, and Z' are known and may be prepared by methods described in the following list of patents and publications which are incorporated herein by reference:

U.S. Pat. No. 4,617,308
U.S. Pat. No. 4,442,101
U.S. Pat. No. 4,496,566
U.S. Pat. No. 4,649,144
U.S. Pat. No. 4,382,937
U.S. Pat. No. 4,341,784
U.S. Pat. No. 4,663,457
U.S. Pat. No. 4,638,067
U.S. Pat. No. 4,668,680
U.S. Pat. No. 4,657,913
U.S. Pat. No. 4,599,334
U.S. Pat. No. 4,571,396
European Patent Application Publication No. 195135
European Patent Application Publication No. 167763
European Patent Application Publication No. 195841
European Patent Application Publication No. 178388
European Patent Application Publication No. 191451
European Patent Application Publication No. 172651
European Patent Application Publication No. 215650

Compounds of formula III wherein X is CCF$_3$, for example, 1-cyclopropyl-6,7-difluoro-1,4-dihydro-oxo-8-(trifluoromethyl)-3-quinolinecarboxylic acid, may be prepared by the following sequence of reactions.

2,4,5-Trifluorobromobenzene (Aldrich) is lithiated and subsequently carboxylated to form the compound 3-bromo-2,5,6-trifluorobenzoic acid. Various lithiating agents such as lithium dialkylamide, for example lithium diisopropylamide, and carbon dioxide in diethyl ether may be used. The reaction proceeds at temperatures from about $-40°$ to $-100°$ C., preferably from about $-60°$ to $-80°$ C. Possible solvents include but are not limited to ether, dimethoxyethane, and tetrahydrofuran. The preferred solvent is tetrahydrofuran.

The carboxylic acid group of the 3-bromo-2,5,6-trifluorobenzoic acid is treated with a fluorinating agent such as, for example, selenium tetrafluoride or sulphur tetrafluoride and hydrogen fluoride forming the compound 1-bromo-2,4,5-trifluoro-3-(trifluoromethyl)benzene. The reaction proceeds for from about 1 to 48 hours at temperatures of about 80° to 150° C. Preferably the reaction time is from about six to eight hours at temperatures from about 120° to 140°.

Subsequently the bromine group of the above compound is treated with a carboxylating agent forming the compound 2,4,5-trifluoro-3-(trifluoromethyl)benzoic acid. Possible carboxylating agents include but are not limited to n-butyl lithium and carbon dioxide, Mg and either CO$_2$ or a chloroformate followed by ester hydrolysis, or other lithium such a MeLi or t-butyl lithium followed by an anhydrous halide salt of a less electropositive metal, then followed either by CO$_2$ or a chloroformate derivative, which would be subsequently hydrolyzed; preferably n-butyl lithium and carbon dioxide are used. This portion of the process proceeds at temperatures from about −40° to −100° C. in ether or tetrahydrofuran. Temperatures from about −70° to −80° are preferred.

The benzoic acid formed above is then treated with a chlorinating agent, an alkyl hydrogen malonate and n-butyl lithium forming the desired alkyl 2,4,5-trifluoro-β-oxo-3-(trifluoromethyl)benzenepropanoate. Various chlorinating agents will be useful such as, for example thionyl chloride, POCl₃, PCl₃, and PCl₅. Brominating agents are also possible such as, for example SOBr₂. Thionyl chloride is the preferred agent used with a dianion of a malonate, such as ethyl hydrogen malonate. The reaction proceeds at temperatures of from about −40° to −100°; preferably from about −70° to −85° C.

The above propanoate is reacted with an alkylorthoformate and acetic anhydride and subsequently with a primary alkylamino group, e.g., cyclopropylamine, forming an ethyl (N-(cyclo)alkylaminomethylene)-3-oxo-3-aryl propanoate derivative. The reactants are preferably ethylorthoformate and cyclopropylamine or ethylamine. The reaction proceeds for about one to six hours at reflux.

The above product is reacted with a base in an organic solvent to cyclize the compound forming alkyl 1-alkyl-6,7-difluoro-8-trifluoromethylquinol-4-one-3-carboxylate, in particular, ethyl 1-cyclopropyl-6,7-difluoro-8-trifluoromethylquinol-4-one-3-carboxylate. A preferred base is an alkali hydride such as sodium hydride and solvents include but are not limited to t-butanol, DMSO or tetrahydrofuran. The reaction occurs at temperatures from about −20° to 100° C.

The quinolone is then deesterified forming the corresponding carboxylic acid. Useful reactants are chlorotrimethylsilane and sodium iodide in acetonitrile. Hydrogen chloride in acetic acid is also useful. The deesterification occurs at reflux which in the case of acetonitrile would be at about 80° C. The reaction time is from two to six hours.

A starting material of the formula Z' wherein Z' is

may be prepared by the following reaction steps.

2,6-Diaminoheptanedioic acid is esterified, preferably with thionyl chloride and methanol, to form the corresponding 2,6-diaminoheptanedioic acid dimethyl ester hydrochloride. The 2,6-diaminoheptanedioic acid may be substituted at the 3-, 4-, or 5-positions each independently by an alkyl, preferably by a methyl group. The reaction proceeds at reflux and then is stirred for from 10 to 20 hours or overnight at room temperature.

The esterified compound is then reacted with a trialkylamine and an alcohol, such as for example, 1-pentanol to form the corresponding 6,8-diazabicyclo[3.2.2]nonane-7,9-dione. The triethylamine is the preferred reactant. A dilute solution is used. It is heated under reflux for as long as four days.

The dione formed is reacted with an alkali metal hydride, preferably, sodium hydride, and an unsubstituted benzylhalide to form the corresponding 6,8-bis(substituted benzyl)-6,8-diazabicyclo[3.2.2]nonane-7,9-dione. Preferably bromomethylbenzene or an α-methyl benzyl halide such as chlorine, bromine, or iodine is used.

The above bis benzylated dione-containing compound is then reduced to the corresponding 6,8-bis(substituted benzyl)-6,8-diazabicyclo[3.2.2]nonane with lithium aluminum hydride in tetrahydrofuran, diglyme, diethylether, or dioxane. Tetrahydrofuran is the preferred solvent. The reduced compound is subsequently debenzylated by catalytic hydrogenation with, preferably, palladium on carbon, to form a desired 6,8-diazabicyclo[3.2.2]nonane, hydrochloride. The reaction occurs in methanol and water in a ratio of about 2:1.

The compounds of the present invention having an additional α-amino acid group are potent antibacterial agents against both gram-positive and gram-negative bacteria. The unexpected advantage found for the present compounds is an enhancement in in vivo activity when administered both orally and subcutaneously. The following table illustrates the advantage of the present compounds by the comparative in vivo data. The reference agents are identical to the exemplified compounds absent the α-amino acid moiety.

TABLE 1

| | In Vivo Activity in Mice PD₅₀ (mg/kg) by Oral (PO) and Subcutaneous (SC) Routes | | | | | |
|---|---|---|---|---|---|---|
| | E. coli | | S. pyogenes | | S. pneumoniae | |
| Compound | PO | SC | PO | SC | PO | SC |
| Enoxacin | 3 | 2 | >100 | 45 | >100 | >100 |
| Reference | | | | | | |
| Reference | 2 | 0.6 | 32 | 14 | 58 | 33 |
| Example 5 | 1.5 | 0.6 | 15 | 7 | 28 | 10 |
| Reference | 16 | 2 | | | 8 | 7 |
| Example 4 | 2.5 | 0.7 | | | 12 | 3 |
| Example 6 (#15) | 1.3 | 0.4 | 22 | 10 | 25 | 12 |

The test was carried out using 8 to 16 mice per dose level according to the well-known method described in Antimicrobial Agents and Chemotherapy, 2, 1972, pp. 89–94 by Heifetz, et al., and the values recorded as PD₅₀ in mg/kg. PD₅₀ means median protective dose.

The compounds of the invention can be prepared and administered in a wide variety of oral, parenteral, and topical dosage forms. It will be obvious to those skilled in the art that the following dosage forms may comprise as the active component, either a compound of formula I, an optical isomer therof, or a corresponding pharmaceutically acceptable salt of a compound of formula I.

For preparing pharmaceutical compositions from the compounds described by this invention, inert, pharmaceutically acceptable carriers can be either solid or liquid. Solid form preparations include powders, tablets, dispersible granules, capsules, cachets, suppositories, and ointments. A solid carrier can be one or more substances which may also act as diluents, flavoring agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparation included solutions, suspensions, and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqeuous suspension suitable for oral use can be made by dispersing the finely divided active component in water with viscous material, i.e., natural or synthetic gums, resins, methyl cellulose, sodium caboxymethyl cellulose, and other well-known suspending agents.

Ointment preparations contain heavy metal salts of a compound of formula I with a physiologically acceptable carrier. The carrier is desirably a conventional water-dispersible hydrophilic or oil-in-water carrier, particularly a conventionally semi-soft or cream-like water-dispersible or water soluble, oil-in-water emulsion which may be applied to an affected burn surface or infected surface with a minimum of discomfort. Suitable compositions may be prepared by merely incorporating or homogeneously admixing finely divided compounds with the hydrophilic carrier or base or ointment.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, powders in vials or ampules, and ointments in tubes or jars. The unit dosage form can also be a capsule, cachet, tablet, gel, or cream itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate methods for preparing the compounds of the invention.

EXAMPLE 1

7-[3-[(2-Amino-1-oxopropyl)amino]-1-pyrrolidinyl]-1-cyclopropyl-6,8-difluoro-1,4-dihydro-4-oxo-3-quinolinecarboxylic acid, monohydrochloride

[1-Methyl-2-oxo-2-[(1-(phenylmethyl)-3-pyrrolidinyl)amino]ethyl]carbamic acid 1,1-dimethylethyl ester (Mixture of isomers)

To a solution of 9.46 g (50 mmol) of t-butoxycarbonylamino-L-alanine (Sigma) in 100 ml of acetonitrile was added 8.1 g (50 mmol) of 1,1'-carbonyldiimidazole. After gas evolution ceased, the reaction mixture was heated at 60° for one hour and allowed to stand at room temperature for 18 hours. The reaction was cooled to 0° and treated with 8.8 g (150 mmole) of 1-benzyl-3-pyrrolidinamine (J. Med. Chem., 24, 1229 (1981)). The reaction was stirred at room temperature for three hours and the solvent was removed in vacuo. The residue was dissolved in ethyl acetate, washed with water, dried (MgSO$_4$) and evaporated in vacuo to give 16.1 g of the title compound with crystallized on standing and had, mp 83°–85°.

[1-Methyl-2-oxo-2-[(3-pyrrolidinyl)amino]ethyl]-carbamic acid 1,1-dimethylethyl ester (mixture of isomers)

A solution of 6.9 g (20 mmol) of [1-methyl-2-oxo-2-[(1-(phenylmethyl)-3-pyrrolidinyl)amino]ethyl]-carbamic acid 1,1-dimethylethyl ester in 100 ml of methanol was treated with 1.0 g of 20% palladium on carbon and shaken in a hydrogen atmosphere at pressures of 33.6 to 52.7 psi and temperatures of 23.5°–27.0 for 18 hours. The catalyst was removed by filtration and the solvent evaporated to give 5.0 g of the title compound as a viscous liquid.

1-Cyclopropyl-7-[3-[[2-[[(1,1-dimethylethoxy)carbonyl]amino]-1-oxopropyl]amino]-1-pyrrolidinyl]-6,8-difluoro-1,4-dihydro-4-oxo-3-quinolinecarboxylic acid (mixture of isomers)

A suspension of 1.4 g (50 mmol) of 1-cyclopropyl-6,7,8-trifluoro-1,4-dihydro-4-oxoquinoline-3-carboxylic acid, 1.92 g (7.5 mmol) of [1-methyl-2-oxo-2-[(3-pyrrolidinyl)amino]ethyl]-carbamic acid 1,1-dimethylethyl ester, 1.5 g (15 mmol) of triethylamine and 75 ml of acetonitrile was heated at reflux for five hours. The solvent was removed in vacuo and the residue was partitioned between chloroform/water (250 ml each) and acidified to pH 2.0 at 0° with 6.0M hydrochloric acid. The solid was removed by filtration, washed with water and dried in vacuo to give 2.4 g of the title compound, mp 185°–187°.

7-[3-[(2-Amino-1-oxopropyl)amino]-1-pyrrolidinyl]-1-cyclopropyl-6,8-difluoro-1,4-dihydro-4-oxo-3-quinolinecarboxylic acid, monohydrochloride A solution of 2.3 g of (4.4 mmol) of 1-Cyclopropyl-7-[3-[[2-[[(1,1-dimethylethoxy)carbonyl]amino]-1-oxopropyl]amino]-1-pyrrolidinyl]-6,8-difluoro-1,4-dihydro-4-oxo-3-quinolinecarboxylic acid in a mixture of 25 ml of 1.0M hydrochloric acid and 25 ml of ethanol was heated at reflux for two hours. The mixture was evaporated to dryness in vacuo and the residue was triturated with ethanol/ether (100 ml/1:1). The solid was removed by filtration, washed with ethanol/ether, ether and dried in vacuo to give 1.6 g of the title compound, mp 238°–240°.

EXAMPLE 2

An Enantioselective Synthesis of Both [S-R*,S*]-and [S-(R*,R*)]-7-[3-[(2-Amino-1-oxopropyl)amino]-1-pyrrolidinyl]-1-cyclopropyl-6,8-difluoro-1,4-dihydro-4-3-quinolinecarboxylic acid, monohydrochloride

(S)-3-Hydroxypyrrolidine

A solution of 22.5 g (105 mmol) of 1-benzyl-3(S)-pyrrolidinol (J. Am. Chem. Soc., 1986, 108, 2049) hydrochloride in 400 ml of methanol was treated with 2.0 g of 20% palladium on carbon and shaken in an atmosphere of hydrogen at temperatures of 23°–26.5° C. and pressures of 48.4–51.2 psi for 21 hours. The catalyst was removed by filtration through Celite and the solvent was removed in vacuo to give 12.9 g of the title compound as a light yellow oil.

(R)-3-Hydroxypyrrolidine

The above procedure was followed using 30.4 g (142 mmol) of 1-benzyl-3(R)-pyrrolidinol (J. Am. Chem. Soc., 1986, 108, 2049) hydrochloride, 600 ml of methanol, and 3.0 g of 20% palladium on carbon to give 14.8 g of the title compound as a light yellow oil.

(R)-3-Hydroxy-1-pyrrolidinecarboxylic acid, phenylmethyl ester

A solution of 10.2 g (82.6 mmol) of R-3-hydroxypyrrolidine hydrochloride (Chem. Letts., 1966, pp 893–6) in 50 ml of water was cooled to 0° and treated with 22.5 ml (90 mmol) of 4.0N sodium hydroxide. The neutral solution was treated dropwise with 15.6 g (86 mmol) of carbobenzyloxy chloride maintaining the pH at 11.0±0.5 by the dropwise addition of 87 ml of 1.0N sodium hydroxide and the temperature below 5° with a salt-ice bath. When the addition was complete, the mixture was stirred at 5° for two hours and stored at 5° for 18 hours. The reaction mixture was saturated with sodium chloride and extracted with ethyl acetate (2×500 ml). The combined organic layers were washed with 1.0N sodium hydroxide (4×50 ml), water, dried (MgSO₄) and evaporated in vacuo to give 17.5 of the title compound.

(S)-3-Hydroxy-1-pyrrolidinecarboxylic acid, phenylmethyl ester

When the above procedure was repeated using 12.4 g (0.1 mol) of (S)-3-hydroxypyrrolidine hydrochloride, the yield of the title compound was 20.1 g.

(R)-3-[(Methylsulfonyl)oxy]-1-pyrrolidinecarboxylic acid, phenylmethyl ester A solution of 17.5 g (84 mmol) of (R)-3-hydroxy-1-pyrrolidinecarboxylic acid, phenylmethyl ester in 150 ml of dry pyridine was cooled to 5° and treated dropwise with 11.5 g (0.1 mol) of methanesulfonyl chloride keeping the temperature at 5°. The reaction mixture was stirred at 5° for two hours and stored at 5° for 18 hours. The reaction mixture was allowed to warm to room temperature over three hours and the solvent was then removed in vacuo. The residue was partitioned between ethyl acetate/water (500 ml each) and the aqueous layer was reextracted with ethyl acetate. The combined organic layers were washed with water, dried (MgSO₄) and evaporated in vacuo to give 21.2 g of the title compound.

(S)-3-[(Methylsulfonyl)oxy]-1-pyrrolidinecarboxylic acid, phenylmethyl ester When the above reaction was run using 19.7 g (89 mmol) of the (S)-isomer, the yield of the title compound was 26.2 g.

(S)-3-Azido-1-pyrrolidinecarboxylic acid, phenylmethyl ester

A solution of 20.5 g (72 mmol) of (R)-3-[(methylsulfonyl)oxy]-1-pyrrolidinecarboxylic acid, phenylmethyl ester in 100 ml of dry N,N-dimethylformamide was treated with 6.5 g (0.1 mol) of sodium azide and heated at 90° for four hours. The solvent was removed in high vacuo at 50° and the residue was partitioned between ethyl acetate/water (250 ml each). The aqueous layer was reextracted with ethyl acetate and the combined organic fractions were washed with water, dried (MgSO₄) and evaporated in vacuo to give 16.2 g of the title compound.

(R)-3-Azido-1-pyrrolidinecarboxylic acid, phenylmethyl ester

When the above reaction was run using 21.0 g (70 mmol) of the S-isomer, the yield of the title compound was 15.2 g.

(S)-3-Amino-1-pyrrolidinecarboxylic acid, phenylmethyl ester

A solution of 14.7 g (60 mmol) of (S)-3-azido-1-pyrrolidinecarboxylic acid, phenylmethyl ester in 200 ml of methanol was treated with 1.0 g of Raneynickel and shaken in a hydrogen atmosphere at pressures of 49.5–51 psi and temperatures of 25.3°–29.4° for nine hours. The catalyst was removed by filtration and the solvent was removed in vacuo to give 13.2 g of the title compound.

(R)-3-Amino-1-pyrrolidinecarboxylic acid, phenylmethyl ester

When the above reaction was run using 15.1 g (61 mmol) of the (R)-isomer, the yield of the title compound was 13.4 g.

(S)-3-[[(1,1-Dimethylethoxy)carbonyl]amino]-1-pyrrolidinecarboxylic acid, phenylmethyl ester To a solution of 13.7 g (60 mmol) of (S-3-amino-1-pyrrolidinecarboxylic acid, phenylmethyl ester in a mixture of 59 ml of 1.0N sodium hydroxide and 90 ml of t-butanol was added dropwise a solution of 13.1 g (60 mmol) of di-tert-butyl dicarbonate in 20 ml of t-butanol keeping the temperature below 40°. The reaction was allowed to come to room temperature over 18 hours and the t-butanol was evaporated in vacuo. The residue was partitioned between ethyl acetate/water (250 ml of each) and the aqueous layer was reextracted with ethyl acetate (250 ml). The combined ethyl acetate layers were washed with water, dried (MgSO$_4$), filtered, and evaporated in vacuo to give 18.2 g of the title compound, mp 124°–125°.

(R)-3-[[(1,1-Dimethylethoxy)carbonyl]amino]-1-pyrrolidinecarboxylic acid, phenylmethyl ester When the above reaction was run using 17.6 g (80 mmol) of (R)-3-amino-1-pyrrolidinecarboxylic acid, phenylmethyl ester, the yield of the title compound was 24.8 g.

(S)-3-[[(1,1-Dimethylethoxy)carbonyl]amino]pyrrolidine

A solution of 17.7 g (55.2 mmol) of (S)-3-[[(1,1-dimethylethoxy)carbonyl]amino]-1-pyrrolidinecarboxylic acid, phenylmethyl ester, in 400 ml of methanol was treated with 2.0 g of 20% palladium on carbon and shaken in an atmosphere of hydrogen at temperatures of 22°–26.5° and pressures of 45–50.5 psi for one hour. The solvent was removed in vacuo to give 10.1 g of the title compound.

(R)-3-[[(1,1-Dimethylethoxy)carbonyl]amino]pyrrolidine

When the above reaction was run using 22.4 g (70 mmol) of (R)-3-[[(1,1-dimethylethoxy)carbonyl]amino]-1-pyrrolidinecarboxylic acid, phenylmethyl ester, the yield of the title compound was 12.5 g.

(S)-1-Cyclopropyl-7-[3-[[(1,1-dimethylethoxy)carbonyl]amino]-1-pyrrolidinyl]-6,8-difluoro-1,4-dihydro-4-oxo-3-quinolinecarboxylic acid, ethyl ester A solution of 12.5 g (40 mmol) of 1-cyclopropyl-6,7,8-trifluoro-1,4-dihydro-4-oxo-3-quinolinecarboxylic acid, ethyl ester, 8.9 g (48 mmol) of (S)-3-[[(1,1-dimethylethoxy)carbonyl]amino]pyrrolidine, 8.1 g (80 mmol) of triethylamine and 75 ml of acetonitrile was heated at reflux for 18 hours. The reaction mixture was cooled to 5° and the solid was removed by filtration, washed with acetonitrile, ether and dried in vacuo to give 19.0 g of the title compounds, mp 148°–151°.

(R)-1-Cyclopropyl-7-[3-[[(1,1-dimethylethoxy)carbonyl]amino]-1-pyrrolidinyl]-6,8-difluoro-1,4-dihydro-4-oxo-3-quinolinecarboxylic acid, ethyl ester When the above reaction was run using 15.6 g (50 mmol) of 1-cyclopropyl-6,7,8-trifluoro-1,4-dihydro-4-oxo-3-quinolinecarboxylic acid, ethyl ester, 10.2 g (55 mmol) of (R)-3-[[(1,1-dimethylethoxy)carbonyl]amino]pyrrolidine, 10.1 g (0.1 mol) triethylamine and 100 ml of acetonitrile, the yield of the title compound was 23.8 g.

(S)-7-[3-(Amino)-1-pyrrolidinyl]-1-cyclopropyl-6,8-difluoro-1,4-dihydro-4-oxo-3-quinolinecarboxylic acid, ethyl ester A solution of 23.9 g (50 mmol) of (S)-1-cyclopropyl-7-[3-[[(1,1-dimethylethoxy)carbonyl]amino]-1-pyrrolidinyl]-6,8-difluoro-1,4-dihydro-4-oxo-3-quinoline carboxylic acid, ethyl ester in 150 ml of trifluoroacetic acid was stirred at room temperature for four hours. The solvent was removed in vacuo and the residue was triturated with 5% sodium bicarbonate. The solid was removed by filtration, washed 5% sodium bicarbonate, water and dried in vacuo to give 17.8 g of the title compound, mp 227°–228°.

(R)-7-[3(Amino)-1-pyrrolidinyl]-1-cyclopropyl-6,8-difluoro-1,4-dihydro-4-oxo-3-quinolinecarboxylic acid, ethyl ester When the above reaction was run using 19.1 g (40 mmol) of (R)-1-cyclopropyl-7-[3-[[(1,1-dimethylethoxy)carbonyl]amino]-1-pyrrolidinyl]-6,8-difluoro-1,4-dihydro-4-oxo-3-quinolinecarboxylic acid, ethyl ester, the yield of the title compound was 14.0 g.

[S-(R*,R*)]-1-Cyclopropyl-7-[3-[[2-[[(1-dimethylethoxy)carbonyl]amino]-1-oxopropyl]amino]-1-pyrrolidinyl]-6,8-difluoro-1,4-dihydro-4-oxo-3-quinolinecarboxylic acid, ethyl ester A solution of 8.76 g (50 mmol) of N-t-butoxy-L-alanine, 5.1 g (50 mmol) of N-methylmorpholine and 100 ml of acetonitrile was cooled to −20° and treated dropwise with 6.9 g (50 mmol) of isobutyl chloroformate keeping the temperature below −10°. The resulting turbid mixture was stirred at −10±5° for one hour and treated with a solution of 18.9 g (50 mmole) of (S)-7-[3-(amino)-1-pyrrolidinyl]-1-cyclopropyl-6,8-difluoro-1,4-dihydro-4-oxo-3-quinolinecarboxylic acid, ethyl ester, in 100 ml of methylene chloride.

The reaction was stirred at 0° for one hour and allowed to come to room temperature where it was stirred for eight hours. The solvent was removed in vacuo and the residue was triturated with water. The solid was removed by filtration, washed with water and dried in vacuo to give 25.2 g of the title compound, mp 100°–105°.

[R-(R*,S*)]-1-Cyclopropyl-7-[3-[[2-[[(1-dimethylethoxy)carbonyl]amino]-1-oxopropyl]amino]-1-pyrrolidinyl]-6,8-difluoro-1,4-dihydro-4-oxo-3-quinolinecarboxylic acid, ethyl ester When the above reaction was run using 7.0 g (40 mmol) of N-t-butoxy-L-alanine, 4.1 g (40 mmol) of N-methylmorpholine, 5.5 g (40 mmol) of isobutyl chloroformate, 15.1 g (40 mmol) of (R)-7-[3-(amino)-1-pyrrolidinyl]-1-cyclopropyl-6,8-difluoro-1,4-dihydro-4-oxo-3-quinolinecarboxylic acid, ethyl ester in a total 100 ml of acetonitrile and 100 ml of methylene chloride, the yield of the title compound was 19.6 g.

[S-(R*,R*)]-7-[3-[(2-Amino-1-oxopropyl)amino]-1-pyrrolidinyl]-1-cyclopropyl-6,8-difluoro-1,4-dihydro-4-oxo-3-quinolinecarboxylic acid, monohydrochloride A solution of 27.4 g (50 mmol) of [S-(R*,R*)]-1-cyclopropyl-7-[3-[[2-[[(1-dimethylethoxy)carbonyl]amino]-1-oxopropyl]amino]-1-pyrrolidinyl]-6,8-difluoro-1,4-dihydro-4-oxo-3-quinolinecarboxylic acid, ethyl ester in 200 ml of ethanol and 100 ml of 1.0M hydrochloric acid was heated at reflux for four hours. The solvent was removed in vacuo and the residue was triturated with 100 ml of a mixture of ethanol/ether (1:1). The solid was removed by filtration, washed with ethanol/ether (1:1), ether and dried in vacuo to give 17.9 g of the title compound, mp 127°–130°.

[R-(R*,S*)]-7-[3-[(2-Amino-1-oxopropyl)amino]-1-pyrrolidinyl]-1-cyclopropyl-6,8-difluoro-1,4-dihydro-4-oxo-3-quinolinecarboxylic acid, monohydrochloride When the above reaction was run using 16.4 g (30 mmol) of [R-(R*,S*)]-1-cyclopropyl-7-[3-[[2-[[(1-dimethylethoxy)carbonyl]amino]-1-oxopropyl]-amino]-1-pyrrolidinyl]-6,8-difluoro-1,4-dihydro-4-oxo-3-quinolinecarboxylic acid, ethyl ester, 60 ml of 1.0M hydrochloric acid and 125 ml of ethanol, the yield of the title compound was 10.4 g, mp 210°-214°.

EXAMPLE 3

[R-(R*,S*)]-7-[3[(2-Amino-1-oxo-3-phenylpropyl)amino]-1-pyrrolidinyl]-1-cyclopropyl-6-fluoro-1,4-dihydro-4-oxo-1,8-naphthyridine-3-carboxylic acid

[R]-2-[1-(Phenylmethyl)-3-pyrrolidinyl]-1H-isoindole-1,3(2H)-dione

To a suspension of 8.9 g (50 mmol) of (S)-1-phenylmethyl-3-hydroxypyrrolidine [Synth. Commun., 15, 587 (1985)], 9.8 g (50 mmol) of phthalimide, 13.1 g (50 mmol) of triphenylphosphine and 100 ml of tetrahydrofuran was added, dropwise, a solution of 8.8 g (50 mmol) of diethyl azodicarboxylate at room temperature. The reaction was stirred for 18 hours and the solvent was removed in vacuo. The residue was triturated with ether and the solid was removed by filtration and chromatographed on silica gel (E. Merck-240-400 mesh) eluting with chloroform/ethyl acetate (80:20). Fractions were combined based on thin layer chromatography and evaporated in vacuo to give 12.1 g of the title compound.

[R]-1-(Phenylmethyl)-3-pyrrolidinamine

A solution of 30.6 g (0.1 mol) of [R]-2-[1-(phenylmethyl)-3-pyrrolidinyl]-1H-isoindole-1,3(2H)-dione in 300 ml of methanol was treated with 6.4 g (0.2 mol) of hydrazine. The reaction was stirred at room temperature for 18 hours and treated with 12.5 ml (0.15 mol) of concentrated hydrochloric acid. The solid was removed by filtration; the precipitate was washed with ethanol and the filtrate evaporated in vacuo. The residue was dissolved in water, made basic with 20% sodium hydroxide saturated with sodium chloride and extracted with ether (3×250 ml). The combined ether layers were washed with saturated sodium chloride solution, dried (MgSO₄), filtered and evaporated in vacuo. The residue was distilled in high vacuo to give 14.4 g of the title compound, bp 86°-87°/0.15 mm.

[R-(R*,S*)]-[1-Phenylmethyl-2-oxo-2-[(1-(phenylmethyl)-3-pyrrolidinyl)amino]ethyl]carbamic acid, 1,1-dimethylethyl ester A solution of 13.3 g (50 mmol) of N-t-butoxy-L-phenylalanine, 5.1 g (50 mmol) of N-methylmorpholine and 100 ml of acetonitrile was cooled to −20° and treated dropwise with 6.9 g (50 mmol) of isobutyl chloroformate keeping the temperature below −10°. The resulting turbid mixture was stirred at −10±5° for one hour and treated with a solution of 8.8 g (50 mmol) of [R]-1-(phenylmethyl)-3-pyrrolidinamine in 50 ml of acetonitrile. The reaction was stirred at 0° for one hour and allowed to come to room temperature where it was stirred for eight hours. The solvent was removed in vacuo and the residue was partitioned between ethyl acetate and water. The organic layer was washed with water, dried (MgSO₄), filtered and evaporated in vacuo to give 17.7 g of the title compound.

[R-(R*,S*)]-[1-Phenylmethyl-2-oxo-2-[(3-pyrrolidinyl)amino]ethyl]carbamic acid, 1,1-dimethylethyl ester A solution of 21.2 g (50 mmol) of [R-(R*,S*)]-[1-phenylmethyl-2-oxo-2-[(1-(phenylmethyl)-3-pyrrolidinyl)amino]ethyl]carbamic acid, 1,1-dimethylethyl ester in 200 ml of methanol was treated with 1.0 g of 20% palladium on carbon and shaken in a hydrogen atmosphere at pressures of 32.5-53.4 psi and temperatures of 23.0°-27.5° for 18 hours. The catalyst was removed by filtration and the solvent was removed in vacuo to give 16.3 g of the title compound.

[R-(R*,S*)]-1-Cyclopropyl-7-[3-[[2-[[(1,1-dimethylethoxy)carbonyl]amino]-1-oxo-3-phenylpropyl]amino]-1-pyrrolidinyl]-6-fluoro-1,4-dihydro-4-oxo-1,8-naphthyridine-3-carboxylic acid A suspension of 14.1 g (50 mmol) of 7-chloro-1-cyclopropyl-6-fluoro-1,4-dihydro-4-oxo-1,8-naphthyridine-3-carboxylic acid, 18.3 g (55 mmol) of [R-(R*,S*)]-[1-phenylmethyl-2-oxo-2-[(3-pyrrolidinyl)amino]ethyl]carbamic acid 1,1-dimethylethyl ester, 15.2 g (0.15 mol) of triethylamine and 200 ml of acetonitrile was heated at reflux for four hours. The solvent was removed in vacuo and the residue was dissolved in methylene chloride and washed with 100 ml of cold 1.0M hydrochloric acid and then water. After drying (MgSO₄) and filtering, the solvent was removed in vacuo to give 26.2 g of the title compound.

[R-(R*,S*)]-7-[3-[(2-Amino-1-oxo-3-phenylpropyl)amino]-1-pyrrolidinyl]-1-cyclopropyl-6-fluoro-1,4-dihydro-4-oxo-1,8-naphthyridine-3-carboxylic acid A solution of 14.5 g (25 mmol) of [R-(R*,S*)]-1-cyclopropyl-7-[3-[[2-[[(1,1-dimethylethoxy)carbonyl]amino]-1-oxo-3-phenylpropyl]amino]-1-pyrrolidinyl]-6-fluoro-1,4-dihydro-4-oxo-1,8-napthyridine-3-carboxylic acid, 100 ml of 1.0M hydrochloric acid and 100 ml of ethanol was heated at reflux for three hours. The solution was filtered through a fiber glass pad to clarify and the solvent removed in vacuo. The residue was triturated with 100 ml of ethanol/ether (1:1) and the solid was removed by filtration. After washing with ethanol/ether (2×50 ml-1:1) and ether, the solid was dried in vacuo to give 10.2 g of the title compound, mp 216°-219°.

[S-(R*,R*)]-7-[3-[2-Amino-1-oxo-3-phenylpropyl)amino]-1-pyrrolidinyl]-1-cyclopropyl-6-fluoro-1,4-dihydro-4-oxo-1,8-naphthyridine-3-carboxylic acid, (3a)

When the above sequence of reactions outlined for Example 3 was carried out using (R)-1-phenylmethyl-3-hydroxypyrrolidine, the title compound was achieved, mp 210°-214°.

Using the same sequence of reactions and substituting N-t-butoxy-D-phenylalanine the final products having the [R-(R*,R*)]-(3b) and [S-(R*,S*]-(3c) configurations were achieved.

EXAMPLE 4

7-[3-[[(2-Amino-1-oxypropyl)amino]methyl]-3-methyl-1-pyrrolidinyl]-1-cyclopropyl-6-fluoro-1,4-dihydro-4-oxo-1,8-naphthyridine-3-carboxylic acid monohydrochloride

[1-Methyl-2-[[(3-methyl-1-(phenylmethyl)-3-pyrrolidinyl)methyl]amino]-2-oxoethyl]carbamic acid, 1,1-dimethylethyl ester (mixture of isomers)

A solution of 14.1 g (75 mmole) of t-butoxycarbonyl-L-alanine in 135 ml of dry acetonitrile was treated with 12.5 g (77 mmol) of 1,1′-carbonyldiimidazole. After stirring at room temperature for one hour and gas evolution had ceased, the reaction mixture was heated at 60° for one hour cooled to room temperature and treated with 14.2 g (70 mmol) of 3-methyl-1-(phenylmethyl)-3-pyrrolidinemethanamine. The reaction mixture was stirred at room temperature for 18 hours and the solvent was removed in vacuo. The residue was partitioned between ethyl acetate/water and the organic layer was separated, washed with water, dried (MgSO₄), and evaporated in vacuo to give 23.9 g of the title compound.

[1-Methyl-2-[[(3-methyl-3-pyrrolidinyl)methyl]amino]-2-oxoethyl]carbamic acid, 1,1-dimethylethyl ester (mixture of isomers)

A solution of 23.1 g (61.6 mmol) of [1-methyl-2-[[(3-methyl-1-(phenylmethyl)-3-pyrrolidinyl)methyl]-amino]-2-oxoethyl]carbamic acid, 1,1-dimethylethyl ester in 400 ml of methanol was treated with 3.0 g of 20% palladium on carbon and shaken in a hydrogen atmosphere at temperatures of 22°-26° and pressures of 48.7-53.4 psi for 2.5 hours. The catalyst was removed by filtering through celite and the filtrate was evaporated in vacuo to give 17.0 g of the title compound.

7-[3-[[[2-[[(1,1-dimethylethoxy)carbonyl]amino]-1-oxypropyl]amino]methyl]-3-methyl-1-pyrrolidinyl]-1-cyclopropyl-6-fluoro-1,4-dihydro-4-oxo-1,8-naphthyridine-3-carboxylic acid (mixture of isomers)

A solution of 1.2 g (4.3 mmol) of 7-chloro-1-cyclopropyl-6-fluoro-1,4-dihydro-4-oxo-1,8-naphthyridine-3-carboxylic acid, 2.43 g (8.5 mmol) of [1-methyl-2-[[(3-methyl-3-pyrrolidinyl)methyl]-amino]-2-oxoethyl]carbamic acid, 1,1-dimethylethyl ester, 1.3 g (13 mmol) of triethylamine and 50 ml of acetonitrile was heated at reflux for three hours. The solvent was removed in vacuo and the residue was partitioned between methylene chloride and water.

The organic layer was washed with water, dried (MgSO₄), and evaporated in vacuo to give 2.1 g of the title compound.

7-[3-[[(2-Amino-1-oxypropyl)amino]methyl]-3-methyl-1-pyrrolidinyl]-1-cyclopropyl-6-fluoro-1,4-dihydro-4-oxo-1,8-naphthyridine-3-carboxylic acid monohydrochloride (mixture of isomers)

A suspension of 2.6 g (4.9 mmol) of 7-[3-[[[2-[[(1,1-dimethylethoxy)carbonyl]amino]-1-oxypropyl]amino]-methyl]-3-methyl-1-pyrrolidinyl]-1-cyclopropyl-6-fluoro-1,4-dihydro-4-oxo-1,8-naphthyridine-3-carboxylic acid, 1,1-dimethylethyl ester in 50 ml of ethanol and 50 ml of 1.0M hydrochloric acid was heated at reflux for three hours. The resulting solution was filtered through a fiber glass pad to clarify and the solvent was removed in vacuo. The residue was triturated with ethanol/ether (30 ml each) and the solid was removed by filtration, washed with ethanol/ether (1:1), ether and dried in vacuo to give 1.7 g of the title compound, mp 270°-272°.

Using the sequence of reactions outlined in Example 4, the following compounds were prepared: 7-[3-[[(2-Amino-1-oxopropyl)amino]methyl]-3-methyl-1-pyrrolidinyl]-1-cyclopropyl-6,8-difluoro-1,4-dihydro-4-oxo-3-quinolinecarboxylic acid monohydrochloride, (4a);

7-[3-[[(2-Amino-1-oxopropyl)amino]methyl]-3-methyl-1-pyrrolidinyl]-1-cyclopropyl-6-fluoro-1,4-dihydro-4-oxo-3-quinolinecarboxylic acid monohydrochloride, mp 233°-235°, (4b), and 5-Amino-7-[3-[[(2-amino-1-oxopropyl)amino]-methyl]-3-methyl-1-pyrrolidinyl]-1-cyclopropyl-6,8-difluoro-1,4-dihydro-4-oxo-3-quinolinecarboxylic acid monohydrochloride, (4c).

EXAMPLE 5

7-[3-[(2-Amino-1-oxopropyl)amino]-1-pyrrolidinyl]-1-cyclopropyl-6-fluoro-1,4-dihydro-4-oxo-1,8-naphthyridine-3-carboxylic acid monohydrochloride 1-Cyclopropyl-7-[3-[[2-[[(1,1-dimethylethoxy)carbonyl]amino]-1-oxypropyl]amino]-1-pyrrolidinyl]-6-fluoro-1,4-dihydro-4-oxo-1,8-naphthyridine-3-carboxylic acid (mixture of isomers)

A solution of 1.2 g (4.2 mmol) of 7-chloro-1-cyclopropyl-6-fluoro-1,4-dihydro-4-oxo-1,8-naphthyridine-3-carboxylic acid, 1.7 g (6.6 mmol) of [1-methyl-2-oxo-2-[(3-pyrrolidinyl)amino]ethyl]carbamic acid 1,1-dimethylethyl ester, 1.4 g (13.5 mmol) of triethylamine and 70 ml of acetonitrile was heated at reflux for three hours and then stirred at room temperature for 18 hours. The solvent was removed in vacuo and the residue was partitioned between methylene chloride and water. The organic layer was separated, washed with water, dried (MgSO₄) and evaporated in vacuo to give 2.0 g of the title compound.

7-[3-[(2-Amino-1-oxypropyl)amino]-1-pyrrolidinyl]-1-cyclopropyl-6-fluoro-1,4-dihydro-4-oxo-1,8-naphthyridine-3-carboxylic acid monohydrochloride (mixture of isomers)

A suspension of 2.0 g (4.0 mmol) of 1-cyclopropyl-7-[3-[[2-[[(1,1-dimethylethoxy)carbonyl]amino]-1-oxypropyl]amino]-1-pyrrolidinyl]-6-fluoro-1,4-dihydro-4-oxo-1,8-naphthyridine-3-carboxylic acid (mixture of isomers) in a mixture of 25 ml of ethanol and 25 ml of 1.0M hydrochloric acid was heated at reflux for two hours. The solution was filtered through a fiber glass pad to clarify and the solvent was removed in vacuo. The residue was triturated with ethanol/ether (25 ml each) and the solid was removed by filtration. After washing with ethanol/ether (1:1), ether and drying in vacuo, the yield of the title compound was 1.5 g, mp 222°-224° C.

Using the sequence of reactions outlined in Example 5, the following compounds ere prepared:
7-[3-[(2-Amino-1-oxypropyl)amino]-1-pyrrolidinyl]-1-cyclopropyl-6,8-difluoro-1,4-dihydro-4-oxo-3-quinolinecarboxylic acid monohydrochloride, (5a);
7-[3-[(2-Amino-1-oxopropyl)amino]-1-pyrrolidinyl]-1-cyclopropyl-6-fluoro-1,4-dihydro-4-oxo-3-quinolinecarboxylic acid monohydrochloride, mp 218°-221°, (5b), and
5-Amino-7-[3-[(2-amino-1-oxopropyl)amino]-1-pyrrolidinyl]-1-cyclopropyl-6,8-difluoro-1,4-dihydro-4-oxo-3-quinolinecarboxylic acid monohydrochloride, mp 228°-230°, (5c).

EXAMPLE 6

Using various combinations of chiral amino acids and pyrrolidine side chain enantiomers, the following examples were prepared with the indicated stereochemistry using the previously described routes:
7-[3-[(aminoacetyl)amino]-1-pyrrolidinyl-1-cyclopropyl-6-fluoro-1,4-dihydro-4-oxo-3-quinolinecarboxylic acid hydrochloride (6), mp 208°-210°.
7-[3-[[(2-Amino-1-oxopropyl)amino]methyl]-3-methyl-1-pyrrolidinyl]-1-cyclopropyl-6-fluoro-1,4-dihydro-4-oxo-1,8-naphthyridine-3-carboxylic acid hydrochloride (7), mp 270°-272°.

[R(R*,S*)]- and [S-(R*,R*)]-7-[3-[(2-Amino-1-oxo-propyl)amino]-1-pyrrolidinyl]-1-cyclopropyl-6-fluoro-1,4-dihydro-4-oxo-1,8-naphthyridine-3-carboxylic acid hydrochloride (8), mp 198°-200°.

[R-(R*,R*)]- and [S-(R*,S*)]-7-[3-[(2-Amino-1-oxo-propyl)amino]-1-pyrrolidinyl]-1-cyclopropyl-6,8-difluoro-1,4-dihydro-4-oxo-3-quinolinecarboxylic acid hydrochloride (9), mp 190°-193°.

[R-(R*,S*)- and [S-(R*,R*)]-7-[3-[(2-Amino-1-oxo-propyl)amino]-1-pyrrolidinyl]-1-cyclopropyl-6,8-difluoro-1,4-dihydro-4-oxo-3-quinolinecarboxylic acid hydrochloride (10), mp 200°-202°.

[R-(R*,R*)]- and [S-(R*,S*)]-7-[3-[(2-Amino-1-oxo-propyl)amino]-1-pyrrolidinyl]-1-cyclopropyl-6-fluoro-1,4-dihydro-4-oxo-1,8-naphthyridine-3-carboxylic acid hydrochloride (11), mp 268°-270°.

7-[3-[(Aminoacetyl)amino]-1-pyrrolidinyl]-1-cyclopropyl-6,8-difluoro-1,4-dihydro-4-oxo-3-quinolinecarboxylic acid hydrochloride (12), mp 273°-274°.

5-Amino-7-[3-[[(aminoacetyl)amino]methyl]-3-methyl--pyrrolidinyl]-1-cyclopropyl-6,8-difluoro-1,4-dihydro-4-oxo-3-quinolinecarboxylic acid hydrochloride (13), mp 271°-273°.

7-[3-[[(2-Amino-1-oxo-3-phenylpropyl)amino]-methyl]-3-methyl -1-pyrrolidinyl]-1-cyclopropyl-6,8-difluoro-1,4-dihydro-4-oxo-3-quinolinecarboxylic acid hydrochloride (14), mp 268°-270°.

[S-(R*,R*)]-7-[3-[(2-Amino-1-oxopropyl)amino]-1-pyrrolidinyl]-1-cyclopropyl-6-fluoro-1,4-dihydro-4-oxo-1,8-naphthyridine-3-carboxylic acid, hydrochloride (15), mp 210°-213°.

[R-(R*,S*)]- and [S-(R*,R*)]-7-[3-[(2-Amino-1-oxo-propyl)amino]-1-pyrrolidinyl]-1-cyclopropyl-6-fluoro-1,4-dihydro-4-oxo-3-quinolinecarboxylic acid hydrochloride (16), mp 218°-220°.

7-[3-[[(Aminoacetyl)amino]methyl]-3-methyl-1-pyrrolidinyl]-1-cyclopropyl-6-fluoro-1,4-dihydro-4-oxo-3-quinolinecarboxylic acid hydrochloride, mp 287°-289°.

[R-(R*,S*)]- and [S-(R*,R*)]-5-Amino-7-[3-[[(2-amino-1-oxo-3-phenylpropyl)amino]methyl]-3-methyl-1-pyrrolidinyl]-1-cyclopropyl-6,8-difluoro-1,4-dihydro-4-oxo-3-quinolinecarboxylic acid hydrochloride (17), mp 223°-225°.

7-[3-[[(Aminoacetyl)amino]methyl]-3-methyl-1-pyrrolidinyl]-1-cyclopropyl-6-fluoro-1,4-dihydro-4-oxo-1,8-naphthyridine-3-carboxylic acid hydrochloride (18), mp 297°-300°.

[R-(R*,R*)]- and [S-(R*,S*)]-7-[3-[[(2-Amino-1-oxo-3-phenylpropyl)amino]methyl]-3-methyl-1-pyrrolidinyl]-1-cyclopropyl-6,8-difluoro-1,4-dihydro-4-oxo-3-quinolinecarboxylic acid hydrochloride (18), mp 268°-271°.

[R-(R*,S*)]- and [S-(R*,R*)]-7-[3-[[(2-Amino-1-oxo-3-phenylpropyl)amino]methyl]-3-methyl-1-pyrrolidinyl]-1-cyclopropyl-6-fluoro-1,4-dihydro-4-oxo-3-quinolinecarboxylic acid hydrochloride (20), mp 195°-198°.

[R-(R*,S*)]-5-Amino-7-[3-[(2-amino-1-oxopropyl)-amino]-1-pyrrolidinyl]-1-cyclopropyl-6,8-difluoro-1,4-dihydro-4-oxo-3-quinolinecarboxylic acid hydrochloride (21), mp 267°-272°.

[S(R*,R*)]-5-Amino-7-[3-[(2-amino-1-oxopropyl)-amino]-1-pyrrolidinyl]-1-cyclopropyl-6,8-difluoro-1,4-dihydro-4-oxo-3-quinolinecarboxylic acid hydrochloride (22), mp 228°-230°.

[R-(R*,R*)]- and [S-(R*,S*)]-7-[3-[[(2-Amino-1-oxo-3-phenylpropyl)amino]methyl]-3-methyl-1-pyrrolidinyl]-1-cyclopropyl-6-fluoro-1,4-dihydro-4-oxo-1,8-naphthyridine-3-carboxylic acid hydrochloride (23), mp 190°-195°.

[S-(R*,R*)]- and [R(R*,S*)]-7-[3-[[(2-Amino-1-oxo-3-phenylpropyl)amino]methyl]-3-methyl-1-pyrrolidinyl]-1-cyclopropyl-6-fluoro-1,4-dihydro-4-oxo-1,8-naphthyridine-3-carboxylic acid hydrochloride (24), mp 190°-193°.

[R-[R*,S*)]- and [S-(R*,R*]-7-[3-[(2-Amino-1-oxo-3-phenylpropyl)amino]-1-pyrrolidinyl]-1-cyclopropyl-6-fluoro-1,4-dihydro-4-oxo-1,8-naphthyridine-3-carboxylic acid hydrochloride (25), mp 108°-110°.

[R-(R*,S*)]- and [S-(R*,R*)]-7-[3-[(2-Amino-1-oxo-3-phenylpropyl)amino]-1-pyrrolidinyl]-1-cyclopropyl-6,8-difluoro-1,4-dihydro-4-oxo-3-quinolinecarboxylic acid hydrochloride (26), mp 217°-219°.

[R-(R*,R*)]- and [S-(R*,S*)]-7-[3-[[(2-Amino-1-oxo-propyl)amino]methyl]-3-methyl-1-pyrrolidinyl]-1-cyclopropyl-6-fluoro-1,4-dihydro-4-oxo-1,8-naphthyridine-3-carboxylic acid hydrochloride (27).

[R-(R*,R*)]- and [S-(R*,S*)]-7-[3-[[(2-Amino-1-oxo-propyl)amino]methyl]-3-methyl-1-pyrrolidinyl]-1-cyclopropyl-6,8-difluoro-1,4-dihydro-4-oxo-3-quinolinecarboxylic acid hydrochloride (28).

[R-(R*,S*)]- and [S-(R*,R*)]-7-[3-[[(2-Amino-1-oxo-propyl)amino]methyl]-3-methyl-1-pyrrolidinyl]-1-cyclopropyl-6-fluoro-1,4-dihydro-4-oxo-3-quinolinecarboxylic acid hydrochloride (29).

7-[3-[(Aminoacetyl)amino]-1-pyrrolidinyl]-1-cyclopropyl-6-fluoro-1,4-dihydro-4-oxo-1,8-naphthyridine-3-carboxylic acid hydrochloride (30), mp 158°-160°.

[R-(R*,S*)]- and [S-(R*,R*)-1-Cyclopropyl-7-[3-[(2,6-diamino-1-oxohexyl)amino]-1-pyrrolidinyl]-6-fluoro-1,4-dihydro-4-oxo-3-quinolinecarboxylic acid hydrochloride (31), mp 190°-192°.

[R-(R*,S*)]- and [S-(R*,R*)]-7-[3-[(2-Amino-1-oxo-3-phenylpropyl)amino]-1-pyrrolidinyl]-1-cyclopropyl-6-fluoro-1,4-dihydro-4-oxo-3-quinolinecarboxylic acid hydrochloride (32), mp 197°-200°.

[R-(R*,S*)]- and [S-(R*,R*)]-1-Cyclopropyl-7-[3-[(2,6-diamino-1-oxohexyl)amino]-1-pyrrolidinyl]-6-fluoro-1,4-dihydro-4-oxo-1,8-naphthyridine-3-carboxylic acid dihydrochloride (33), mp 125°-130°.

5-Amino-7-[3-[(aminoacetyl)amino]-1-pyrrolidinyl]-1-cyclopropyl-6,8-difluoro-1,4-dihydro-4-oxo-3-quinolinecarboxylic acid hydrochloride (34).

I claim:

1. A compound of the formula wherein
X is N;
Y is H, F, $NH_2$, or $OR_2$;
Z is

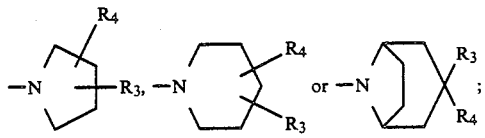

R is H, alkyl of 1-6 carbon atoms or a cation;
$R_1$ is alkyl of 1-6 carbon atoms, haloalkyl in which alkyl has 1-4 carbon atoms, vinyl, cycloalkyl of 3-6 carbon atoms, phenyl, naphthyl or phenyl or naphthyl substituted by halogen, hydroxy, amino or alkyl of 1-4 carbon atoms, indanyl, indolyl, quinolyl, isoquinolyl, 2-, 3-, or 4-pyridine, 2- or 3-thiophene, 2- or 3-furan, 2- or 4-imidazole, 2-oxazole or 2-thiazole;
$R_2$ and $R_3$ are each independently hydrogen or alkyl of 1-4 carbon atoms;
$R_4$ is —$(CR_2R_3)_n$—$NR_2R_5$ in which n is 0, 1, or 2;
$R_5$ is

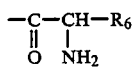

in which $R_6$ is hydrogen, alkyl of 1-10 carbon atoms, alkyl of 1-10 carbon atoms substituted by $OR_2$, $NR_2R_3$, $CO_2H$, $CO_2R_2$, $CONR_2R_3$,

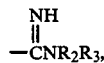

$SR_2$,

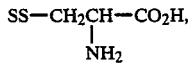

—CN, phenyl, naphthyl or phenyl or naphthyl substituted by halogen, hydroxy, amino, or alkyl of 1-4 carbon atoms, indanyl, indolyl, quinolyl, isoquinolyl, 2-, 3-, or 4-pyridine, 2- or 3-thiophene, 2- or 3-furan, 2- or 4-imidazole, 2-oxazole or 2-thiazole; or $R_6$ is phenyl, p-hydroxyphenyl or taken with the nitrogen atom of the α-amino group is trimethylene or hydroxy substituted trimethylene; and optically active isomer thereof, or a pharmaceutically acceptable acid addition salt thereof.

2. A compound according to claim 1, in which $R_6$ is hydrogen, alkyl of 1-10 carbon atoms or alkyl of 1-10 carbon atoms substituted by $OR_2$, $NR_2R_3$, $CO_2H$, $CO_2R_2$, —$CONR_2R_3$,

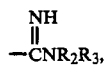

$SR_2$,

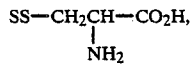

—CN, phenyl, phenyl substituted by halogen, hydroxy, amino or alkyl of 1-4 carbon atoms, 3-indolyl or 4-imidazolyl, or $R_6$ is phenyl, p-hydroxyphenyl or taken with the nitrogen atom of the amino group is trimethylene or hydroxy substituted trimethylene.

3. A compound according to claim 2, in which $R_6$ is hydrogen, alkyl of 1-4 carbon atoms or alkyl of 1-4 carbon atoms substituted by OH, $NH_2$, $CO_2H$, $CONH_2$,

$SR_2$,

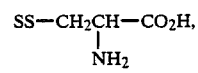

phenyl, p-hydroxyphenyl, 3-indolyl or 4-imidazolyl, or $R_6$ is phenyl, p-hydroxyphenyl or taken with the nitrogen of the α-amino group is trimethylene or hydroxy substituted trimethylene.

4. A compound according to claim 3, wherein $R_1$ is alkyl of 1-3 carbon atoms, 2-fluoroethyl, vinyl, cyclopropyl, phenyl, phenyl substituted by halogen, hydroxy, amino or alkyl of 1-4 carbon atoms.

5. A compound according to claim 4, wherein X is N.

6. A compound according to claim 5, wherein Y is H or $NH_2$.

7. A compound according to claim 6, wherein $R_1$ is ethyl, 2-fluoroethyl, vinyl, or cyclopropyl.

8. A compound according to claim 7, wherein Z is

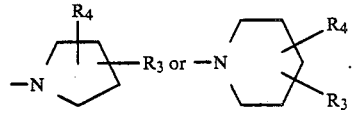

9. A compound according to claim 8, wherein Z is

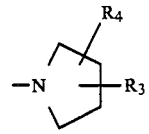

and $R_1$ is cyclopropyl.

10. A compound according to claim 9 and being 7-[3-[(2-amino-1-oxopropyl)amino]-1-pyrrolidinyl]-1-cyclopropyl-6-fluoro-1,4-dihydro-4-oxo-1,8-naphthyridine-3-carboxylic acid or an optical isomer thereof.

11. The [S-(R*,R*)] or the [S-(R*,S*)] isomer of the compound of claim 10.

12. A compound according to claim 9 and being 7-[3-[(aminoacetyl)amino]-1-pyrrolidinyl]-1-cyclopropyl-6-fluoro-1,4-dihydro-4-oxo-1,8-naphthyridine-3-carboxylic acid or an optical isomer thereof.

13. A compound according to claim 9 and being 7-[3-[(2-amino-1-oxo-3-phenylpropyl)amino]-1-pyrrolidinyl]-1-cyclopropyl-6-fluoro-1,4-dihydro-4-oxo-1,8-naphthyridine-3-carboxylic acid or an optical isomer thereof.

14. The [S-(R*,S*)] or the [S-(R*,R*)] isomer of the compound of claim 13.

15. A compound according to claim 9 and being 7-[3-[(2,5-diamino-1,5-dioxopentyl)amino]-1-pyrrolidinyl]-1-cyclopropyl-6-fluoro-1,4-dihydro-4-oxo-1,8-naphthyridine-3-carboxylic acid or an optical isomer thereof.

16. A compound according to claim 9 and being 7-[3-[(2-amino-4-carboxy-1-oxobutyl)amino]-1-pyrrolidinyl]-1-cyclopropyl-6-fluoro-1,4-dihydro-4-oxo-1,8-naphthyridine-3-carboxylic acid or an optical isomer thereof.

17. A compound according to claim 9 and being 7-[3-[(2,6-diamino-1-oxohexyl)amino]-1-pyrrolidinyl]-1-cyclopropyl-6-fluoro-1,4-dihydro-4-oxo-1,8-naphthyridine-3-carboxylic acid or an optical isomer thereof.

18. A compound according to claim 9 and being 7-[3-[(aminophenylacetyl)amino]-1-pyrrolidinyl]-1-cyclopropyl-6-fluoro-1,4-dihydro-4-oxo-1,8-naphthyridine-3-carboxylic acid or an optical isomer thereof.

19. A compound according to claim 9 and being 7-[3-[[(2-amino-1-oxo-3-phenylpropyl)amino]methyl]-3-methyl-b 1-pyrrolidinyl]-1-cyclopropyl-6-fluoro-1,4-dihydro-4-oxo-1,8-naphthyridine-3-carboxylic acid or an optical isomer thereof.

20. A compound according to claim 9 and being 7-[3-[[(2-amino-1-oxopropyl)amino]methyl]-3-methyl-1-pyrrolidinyl]-1-cyclopropyl-6-fluoro-1,4-dihydro-4-oxo-1,8-naphthyridine-3-carboxylic acid or an optical isomer thereof.

21. A compound according to claim 9 and being 7-[3-[[(aminoacetyl)amino]methyl]-3-methyl-1-pyrrolidinyl]-1-cyclopropyl-6-fluoro-1,4-dihydro-4-oxo-1,8-naphthyridine-3-carboxylic acid or an optical isomer thereof.

22. A compound according to claim 9 and being 7-[3-[[(aminophenylacetyl)amino]methyl]-3-methyl-1-pyrrolidinyl]-1-cyclopropyl-6-fluoro-1,4-dihydro-4-oxo-1,8-naphthyridine-3-carboxylic acid or an optical isomer thereof.

23. A compound according to claim 9 and being 7-[3-[[(2-amino-4-carboxy-1-oxobutylamino]methyl]-3-methyl-1-pyrrolidinyl]-1-cyclopropyl-6-fluoro-1,4-dihydro-4-oxo-1,8-naphthyridine-3-carboxylic acid or an optical isomer thereof.

24. A compound according to claim 9 and being 7-[3-[[(2,6-diamino-1-oxohexyl)amino]methyl]-3-methyl-1-pyrrolidinyl]-1-cyclopropyl-6-fluoro-1,4-dihydro-4-oxo-1,8-naphthyridine-3-carboxylic acid or an optical isomer thereof.

25. A compound according to claim 9 and being 7-[3-[[(2,5-diamino-1,5-dioxopentyl)amino]methyl]-3-methyl-1-pyrrolidinyl]-1-cyclopropyl-6-fluoro-1,4-dihydro-4-oxo-1,8-naphthyridine-3-carboxylic acid or an optical isomer thereof.

26. A pharmaceutical composition comprising an antibacterially effective amount of a compound according to claim 1 together with a carrier or excipient.

27. A method of treating bacterial infections comprising administering to a host suffering therefrom a pharmaceutical composition according to claim 26 in unit dosage form.

* * * * *

UNITED STATES PATENT AND TRADEMARK OFFICE
CERTIFICATE OF CORRECTION

PATENT NO. : 4,851,418

DATED : July 25, 1989

INVENTOR(S) : Joseph Peter Sanchez

It is certified that error appears in the above—identified patent and that said Letters Patent is hereby corrected as shown below:

Column 25, Claim 19, line 16 - "methyl-b  1-pyrrolidinyl]-" should read --methyl-1-pyrrolidinyl]- --.

Signed and Sealed this

Twenty-fourth Day of July, 1990

Attest:

HARRY F. MANBECK, JR.

Attesting Officer

Commissioner of Patents and Trademarks